United States Patent
Agar et al.

(10) Patent No.: US 10,254,151 B2
(45) Date of Patent: Apr. 9, 2019

(54) SYSTEM AND METHOD FOR MEASURING FLUIDS

(71) Applicant: AGAR Corporation Ltd., Grand Cayman (KY)

(72) Inventors: Joram Agar, Grand Cayman (KY); Hector Viale-Rigo Capuzzo, Simonton, TX (US); David Farchy, Bellaire, TX (US)

(73) Assignee: AGAR CORPORATION Ltd., Grand Cayman (KY)

(*) Notice: Subject to any disclaimer, the term of this patent is extended or adjusted under 35 U.S.C. 154(b) by 138 days.

(21) Appl. No.: 15/482,715

(22) Filed: Apr. 8, 2017

(65) Prior Publication Data

US 2017/0292871 A1    Oct. 12, 2017

Related U.S. Application Data

(60) Provisional application No. 62/320,354, filed on Apr. 8, 2016.

(51) Int. Cl.
| | | |
|---|---|---|
| *G01F 23/64* | (2006.01) | |
| *G01N 33/28* | (2006.01) | |
| *G01F 23/76* | (2006.01) | |
| *G01F 23/68* | (2006.01) | |

(52) U.S. Cl.
CPC ............. *G01F 23/64* (2013.01); *G01F 23/68* (2013.01); *G01F 23/76* (2013.01); *G01N 33/2847* (2013.01)

(58) Field of Classification Search
CPC ... F16L 2101/30; F16L 55/26; F16L 2201/30; G01F 23/76; G01F 23/64; G01F 23/68; G01M 3/022
See application file for complete search history.

(56) References Cited

U.S. PATENT DOCUMENTS

| | | | | |
|---|---|---|---|---|
| 1,587,663 | A * | 6/1926 | Lundgren | F28F 11/04 138/91 |
| 2,192,155 | A * | 2/1940 | Schuldt | F16K 7/10 73/40.5 R |
| 3,431,945 | A * | 3/1969 | Robillard | E03F 7/02 138/90 |
| 4,454,761 | A * | 6/1984 | Coulange | G01F 23/68 73/305 |
| 4,503,383 | A |  3/1985 | Agar | |

(Continued)

*Primary Examiner* — David A Rogers
(74) *Attorney, Agent, or Firm* — Craft Chu PLLC; Andrew W. Chu

(57) ABSTRACT

A system and method for measuring fluids include a vessel containing at least two fluids with a drain pipe, a seal housing, a tool assembly, and a float assembly. The seal housing fits onto the drain pipe of existing vessels or tanks, and the tool assembly and float assembly are inserted through the seal housing to the vessel to measure the fluids inside the tank. The tool assembly has a shaft section and a flexible section. The flexible section extends into the vessel and through any bend in the drain pipe so that the system is compatible with retrofitting vessels with different drain pipe shapes. The float assembly can be released from the end of the bent drain pipe to float to the fluid boundary between different fluids in the vessel. The float assembly can also be retracted to safe position within the seal housing.

20 Claims, 3 Drawing Sheets

(56) References Cited

U.S. PATENT DOCUMENTS

| | | | | |
|---|---|---|---|---|
| 4,519,415 A * | 5/1985 | Carn | ................. | F17C 3/022 137/318 |
| 4,608,858 A * | 9/1986 | McKinnon | ............ | G01M 3/022 138/93 |
| 4,876,888 A * | 10/1989 | Ricketts | ................. | G01F 23/04 73/319 |
| 5,201,435 A * | 4/1993 | Harding | ................. | B65D 90/24 220/567.2 |
| 6,218,949 B1 * | 4/2001 | Issachar | ................. | G01F 23/62 340/603 |
| 6,318,581 B1 | 11/2001 | Garton | | |
| 6,351,985 B1 * | 3/2002 | Bedwell | ................. | G01M 3/022 138/90 |
| 6,502,452 B1 * | 1/2003 | Gill | ................. | F16L 55/132 138/90 |
| 6,536,277 B1 * | 3/2003 | Chuang | ................. | G01C 13/002 340/623 |
| 6,634,676 B1 * | 10/2003 | Lampson | ................. | B65D 90/24 220/601 |
| 7,353,704 B2 * | 4/2008 | Clanton | ................. | G01F 23/42 242/615 |
| 7,610,806 B2 * | 11/2009 | Skinner | ................ | G01F 23/2963 73/290 R |
| 8,276,780 B2 * | 10/2012 | Oltman | ..................... | F16L 5/08 220/4.12 |
| 8,904,882 B2 * | 12/2014 | Mertmann | ................. | G01F 1/20 73/1.16 |
| 9,598,665 B1 * | 3/2017 | Barnum | ................. | F16L 23/167 |
| 9,599,571 B2 * | 3/2017 | Penza | ................. | F16K 7/10 |
| 9,933,056 B2 * | 4/2018 | Kiesel | ................. | F16L 55/265 |
| 2004/0206778 A1 | 10/2004 | Floyd et al. | | |
| 2005/0268971 A1 * | 12/2005 | Nasalroad | ............. | F16K 24/046 137/565.13 |
| 2011/0214880 A1 | 9/2011 | Rogers | | |
| 2011/0220227 A1 * | 9/2011 | Gray | ................. | E03B 7/04 137/605 |
| 2013/0036588 A1 | 2/2013 | Agar | | |
| 2015/0153215 A1 * | 6/2015 | Uskert | ................. | G01F 23/72 73/305 |
| 2015/0177050 A1 * | 6/2015 | Taylor | ................. | G01F 23/72 73/305 |

\* cited by examiner

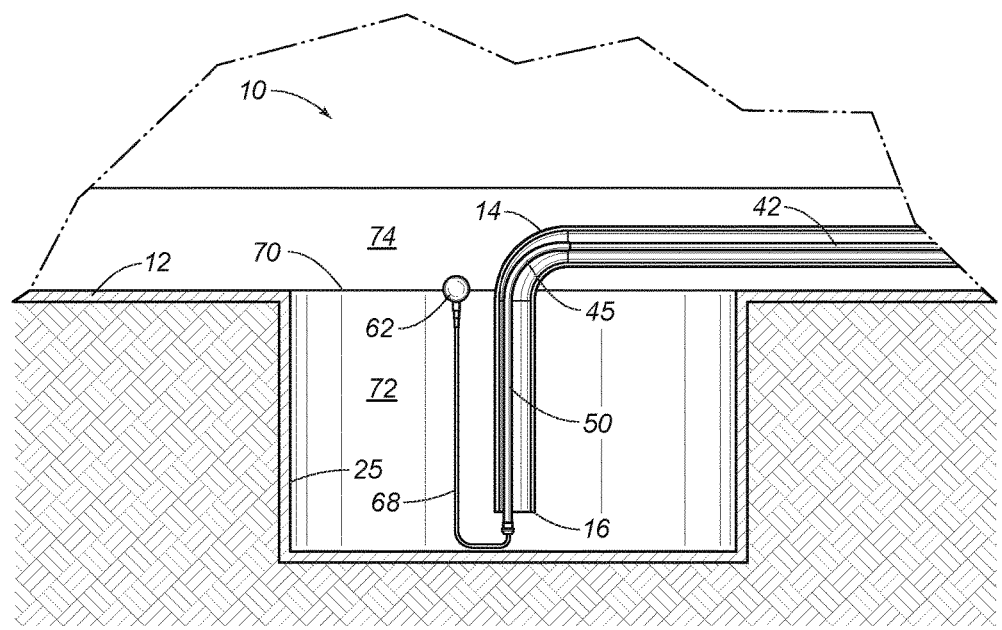
FIG. 4
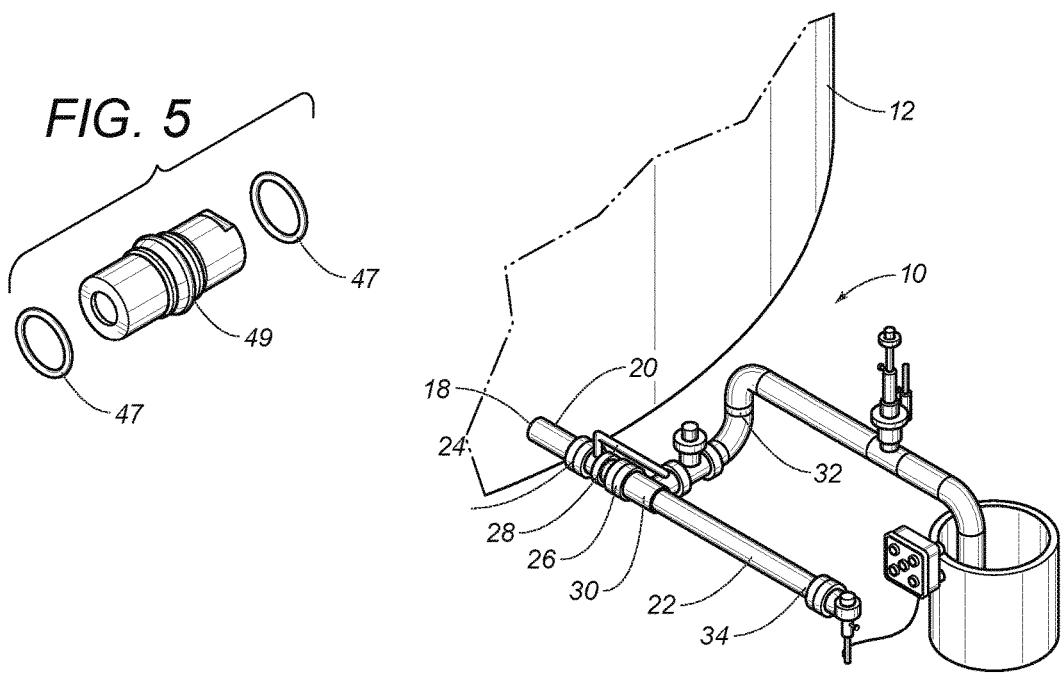
FIG. 5
FIG. 6

SYSTEM AND METHOD FOR MEASURING FLUIDS

CROSS-REFERENCE TO RELATED APPLICATIONS

The present application claims priority under 35 U.S.C. Section 119(e) from U.S. Provisional Patent Application Ser. No. 62/320354, filed on 8 Apr. 2016, entitled "SYSTEM AND METHOD FOR INSTALLING A PROBE IN A TANK".

See also Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to storage vessels. In particular, the present invention relates to a system and method for measuring fluids by installing a probe in a tank containing two different fluids. Even more particularly, the present invention relates to a safe and reliable system and method for determining the amount of each different fluid in a storage tank with a probe without damaging the storage tank.

2. Description of Related Art Including Information Disclosed Under 37 CFR 1.97 and 37 CFR 1.98

Storage vessels containing hydrocarbons, crude oil, feedstocks, intermediates and finished products accumulate water over time at the bottom of the vessels. Standard industry practice is to periodically drain the water from the vessel. Automatic vessel de-watering is also used to drain water. In automatic systems, an interface detector probe and a shut-off valve are installed in a drawline at a location outside the tank. This system is susceptible to oil spillage due to time delay between oil detection in the drawline and shutting off of the control valve. Accumulated water then traps the oil in the drawline, thus requiring a manual restart and subsequent oil spillage. For existing storage vessels, the probe can be installed at a wall of the tank using a welding process known as hot-tapping, which process can be hazardous, dangerous and cumbersome. In addition, once a hot-tapping process is completed, the tank needs to be recertified by regulatory authorities. The present disclosure provides a method for installing a device, such as a detector probe, inside a storage vessel that avoids hot-tapping, improves safety, reduces pollution and can be performed without the need for recertification of the tank.

The prior art inserts a probe through an existing opening from a top of a tank or through a drain pipe near the bottom of the tank. When the drain pipe is bent downward within the tank, a hole must be created in the drain pipe to insert the probe. Prior art systems drill holes into tank structures, permanently altering the integrity and function of the drain pipe and the tank.

It is an object of the present invention to provide an embodiment of a system and method for measuring fluids by installing a probe in a tank without altering the tank.

It is an object of the present invention to provide an embodiment of a system and method for installing a probe while preserving integrity of the tank.

It is an object of the present invention to provide an embodiment of a system and method for installing a probe in any tank having a bent drain pipe.

It is an object of the present invention to provide an embodiment of a system and method for installing a probe in a tank of any size.

It is an object of the present invention to provide an embodiment of a system and method for installing a probe in a tank with drain pipe of any size.

These and other objectives and advantages of the present invention will become apparent from a reading of the attached specification.

BRIEF SUMMARY OF THE INVENTION

Embodiments of the present invention include a system for measuring fluids by installing a probe in a tank or vessel. The probe can be any one or a combination of a float ball, an antenna, and other sensor to detect characteristics of fluid. The system includes a vessel, containing at least two fluids. The vessel has an inlet, an outlet, and a drain pipe. The drain pipe has a first end, a second end, and a tank block valve on the second end. The tank block valve controls fluid flow through the drain pipe. There is a seal housing including a first flanged end connected to the second end of the drain pipe. The seal housing also includes a second flanged end, a seal housing valve between the first flanged end and the second flanged end, and a bypass fitting connected to a bypass flow assembly and a shaft housing. A tool assembly, having a shaft section and a flexible section, removably inserts through the drain pipe and through the seal housing. A float assembly extends through the tool assembly, such that a float ball is at one end of the tool assembly with an antenna element and a means for actuating the float ball is at an opposite end of the tool assembly. A means for connecting the float ball extends between the float ball and the means for actuating the float ball, so that the means for actuating the float ball releases and retracts the float ball by dispensing or gathering the means for connecting the float ball. The length of the shaft housing must fit the float ball, the antenna element, and the flexible section of the tool assembly, when the float ball is released and when the float ball is retracted.

In other embodiments, the vessel can have a sump so that the first end of the drain pipe is positioned in the sump. The drain pipe can have different bends, such as a ninety degree downward bend, so as to account for retrofitting any type of drain pipe in any vessel. In some embodiments, the shaft section is comprised of a plurality of shaft segments for a modular construction, and the flexible section can be formed by metal springs or coils of stainless steel. The embodiments of means for actuating include a reel, spool, pneumatic actuator, compressed air system and a hydraulic actuator. The embodiments of the means for connecting include flexible tubing and coaxial cable. The means for actuating can wind the tubing or cable for dispensing or gathering so as to release or to retract the float ball at the end of the tubing or cable.

The embodiments of the invention include the method of measuring fluids by installing a probe, such as an antenna on a float ball, within a tank or vessel. The method includes filling a vessel with at least two fluids, such as hydrocarbons and water, and settling the at least two fluids in layers so as to form a fluid layer boundary. Then, the seal housing, the tool assembly, and the float assembly are installed in the vessel with the tank block valve closed to prevent fluids from exiting through the drain pipe during installation. Alternatively, the seal housing, the tool assembly, and the float assembly are installed before any fluid is stored in the vessel. The proximal end of the shaft section is set at a bend between the first end and the second end with the flexible section extending through the first end. Then, the float ball is released from the free end of the flexible section and settles at the fluid boundary between at least two fluids in the vessel. From this position, the antenna or other sensor detects characteristics of the two fluids and according to dimensions of the vessel and flow rates through the vessel. In one embodiment, the location of the float ball relative to the vessel determines the respective amounts of each of the two fluids within the vessel.

In embodiments with the shaft section comprised of a plurality of shaft segments, the step of installing includes attaching each shaft segment to an adjacent shaft segment with a shaft connector and repeating until the float ball reaches the bottom of the vessel.

The step of releasing the float ball can include dispensing means for connecting and retracting or gathering means for connecting, such as winding and spooling tubing or using a pneumatic actuator to release coaxial cable.

There are some embodiments with the step of opening the tank block valve and the seal housing valve, so as to allow flow through the drain pipe and the bypass assembly of the seal housing. When a vessel is draining, the system can continue to measure the fluids. Additional valves and sensors in the bypass assembly can be used to verify or confirm the measurements by the system. Alternatively, the tank block valve can be opened with the seal housing valve closed, so that the fluids remain in the vessel without draining through the drain pipe until necessary.

BRIEF DESCRIPTION OF THE SEVERAL VIEWS OF THE DRAWINGS

FIG. 4 is another schematic view of the system and method for measuring fluid by installing a probe in a tank or vessel with a sump.

FIG. 5 is an exploded perspective view of a shaft connector for an embodiment of the shaft section of the tool assembly of the present invention.

FIG. 6 is an upper perspective view of the system of the present invention, including the outside of the vessel and the seal housing.

DETAILED DESCRIPTION OF THE INVENTION

Referring to FIGS. 1-6, the system 10 for measuring fluids provides a safer and more efficient alternative to prior art systems. The alteration of the tank or vessel by hot tapping is no longer necessary, and the delay between detecting the oil in the tank and shutting a control valve is eliminated. The system 10 determines the fluid boundary layer early and without affecting the integrity of the tank, so that the control valve can anticipate closing before oil is released. Additionally, the system 10 has more functionality for measuring different fluid characteristics in addition to the fluid boundary level. Different sensors and the antenna element can form the probe for detecting more than water or oil in the tank or vessel.

Figure 1:
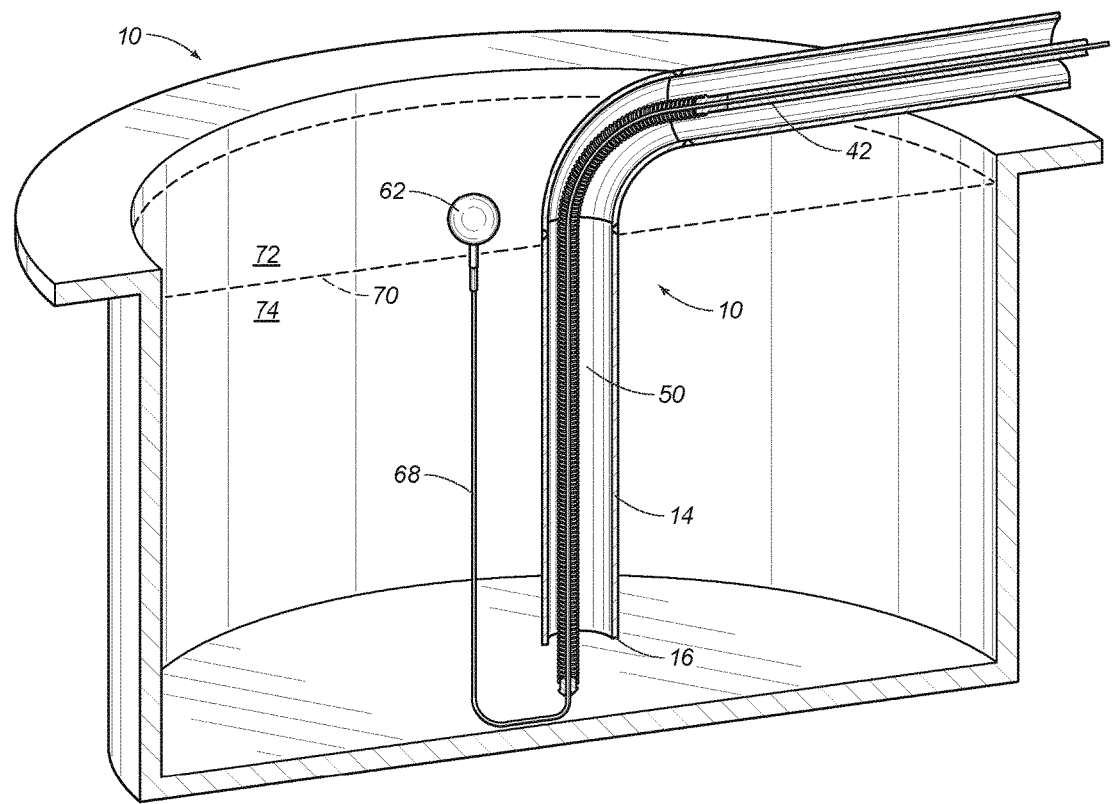
FIG. 1 is a schematic view of the system and method for measuring fluid by installing a probe in a tank or vessel.
Figure 2:
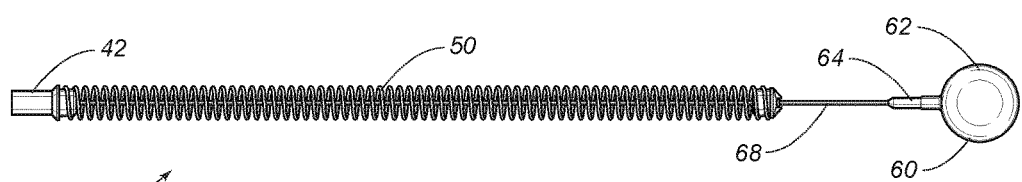
FIG. 2 is a partial isolated elevation view of the tool assembly and the float assembly of the system of the present invention.

FIGS. 1, 4, and 6 show embodiments of the system 10 for measuring fluids by installing a probe in a tank or vessel. The system 10 includes a vessel 12 containing at least two fluids. These fluids are typically hydrocarbon and water, but other fluids are also possible. For hydrocarbons, such as oil, it is important to detect the amount of water in a vessel, so that the water can be drained without draining oil. In the present invention, the vessel 12 is comprised of an inlet, an outlet, and a drain pipe 14 having a first end 16, a second end 18 opposite the first end, and a tank block valve 20 on the second end. The inlet and outlet are not shown because these structures can be anywhere on the vessel 12 for the delivery of fluids into the vessel 12. These fluids can also be removed through the inlet and outlet for any reason, and the inlet and outlet are typically mounted on the top of the vessel. The drain pipe 14 is separate and intended for draining the vessel 12. For example, after using the vessel 12 to store a fluid mixture and after the fluid mixture has been removed from the outlet, there is a need to drain the vessel for to store a different fluid mixture. The residual fluid mixture is an unknown and must be drained so that the vessel can be used again.

The system 10 includes a seal housing 22 shown in FIG. 6. The seal housing 22 relates to retrofitting so that the system 10 is compatible with existing tanks and vessel of different sizes, capacities, and drain pipes. The seal housing 22 connects to the drain pipe 14 so that an existing vessel 12 can be incorporated into the system 10 of the present invention. The seal housing 22 includes a first flanged end 24 connected to the second end 16 of the drain pipe, a second flanged end 26, and a seal housing valve 28 between the first flanged end 24 and the second flanged end 26. The seal housing valve 28 can be closed or opened to allow fluids in the vessel 12 to drain through the drain pipe 14. The embodiment of FIG. 6 shows a bypass fitting 30 having two junctions, a bypass flow assembly 32 in fluid connection with one junction of the bypass fitting, and a shaft housing 34 in fluid connection with a remaining junction of the bypass fitting. The system 10 works to measure fluids, when the vessel 12 is sealed and when the vessel 12 is draining through the drain pipe 14. Additional valves and sensors in the bypass flow assembly 32 of FIG. 6 can be used to verify or confirm the measurements by the system 10.

The first end 16 of the drain pipe 14 is located within the vessel 12 as shown in FIGS. 1 and 4. FIG. 4 shows an alternative embodiment with sump 25. The first end 16 can remain within the sump 25, separate from the main volume of the vessel 12. When, the drain pipe 14 is bent, as in FIGS. 1 and 4, the first end 16 is bent 90 degrees downward from the second end 18. Other bend angles are possible, which allows the system 10 to be compatible with all types of drain pipes in vessels. The second end 18 of the drain pipe 14 is at a distal location outside the vessel, and the tank block valve 20 is positioned between the vessel 12 and the seal housing 22 as shown in FIG. 6.

The system 10 also includes a tool assembly 40 removably inserted through the drain pipe 14 in FIGS. 1-4. The tool assembly 40 includes a shaft section 42 having a distal end 44 and proximal end 46, and a flexible section 50 at the proximal end 46 of the shaft section 42. The flexible section 50 has an anchored end 52 attached to the proximal 46 end of the shaft section 42 and a free end 54 opposite the anchored end 52. In some embodiments shown in FIGS. 3 and 5, the shaft section 42 can be comprised of a plurality of shaft segments 48. The construction is modular such that each shaft segment 48 is in fluid connection with an adjacent shaft segment 48 and attached to a respective adjacent shaft segment by a shaft connector 49. Additionally, FIG. 5 shows a plurality of 0-rings 47 on the ends of each shaft connector 49 for the sealed engagement to respective shaft segments 48. FIGS. 1-4 show embodiments of the flexible section 50 as formed by a spring, metal spring, or stainless steel coil. Any suitably shaped structure with flexibility to bend along the drain pipe 14 can form the flexible section 50.

Figure 3:
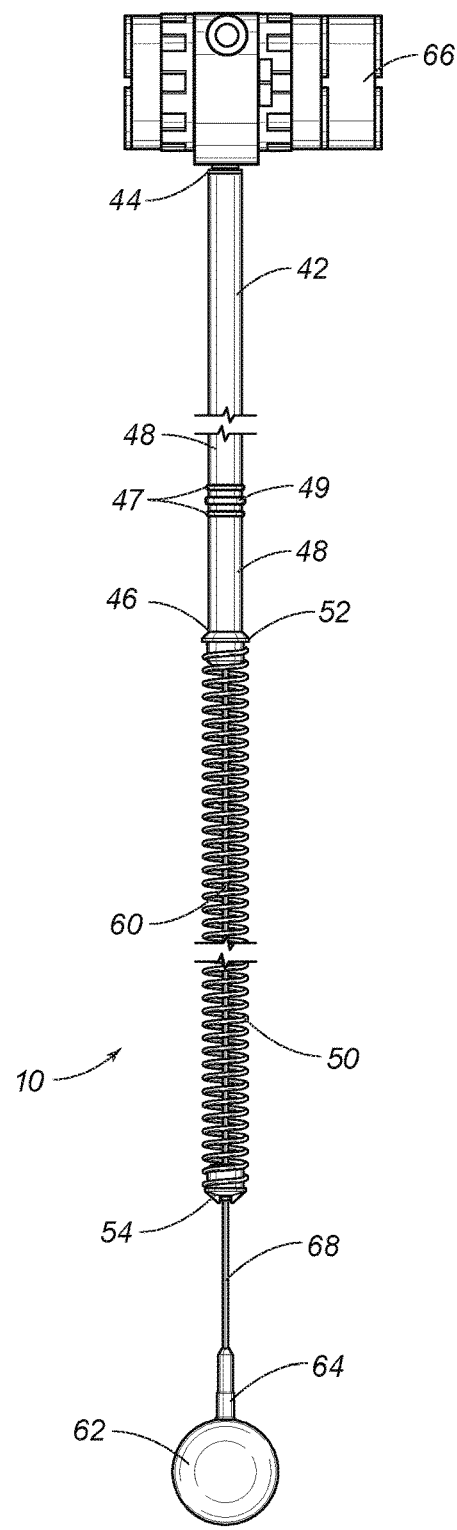
FIG. 3 is a schematic view of the tool assembly and the float assembly of the system of the present invention.

FIGS. 1-4 shown a float assembly 60 extending through the tool assembly 40. The float assembly 60 is generally integrated with the tool assembly 40 because the float assembly 60 extends through the tool assembly 40. There is structural support and protection provided by the tool assembly 40. Embodiments of the float assembly 40 include a float ball 62 releasably engaged to the free end 54 of the flexible section 50, an antenna element 64 attached to the float ball 62, a means for actuating the float ball 66 attached to the distal end 44 of the shaft section 42, and a means for connecting the float ball 68 to the means for actuating the float ball 66. The float ball 62 can withstand tank conditions with temperature resistance and chemical resistance so as not to dissolve or degrade. FIG. 3 shows the means for connecting the float ball 68 extending through the flexible section 50 and the shaft section 40 to the means for actuating the float ball 66. In the present invention, a length of the shaft housing 34 of the seal housing 22 accommodates the float ball 62, the antenna element 64, and the flexible section 50 of the tool assembly 40. The shaft housing 34 must be able to house the flexible section 50, the antenna element 64, and the float ball 62 in a retracted position. The float ball 62 will be friction fit against the seal housing valve 28 and unable to pass through the seal housing 22 to the shaft housing 34. The float ball 62 is larger than the opening of the seal housing valve 28.

In embodiments of the present invention, the means for actuating the float ball 66 is selected from at least one of a reel, spool, a pneumatic actuator, compressed air system, and a hydraulic actuator, and the means for connecting the float ball 68 is selected from at least one of flexible tubing and coaxial cable. The means for actuating 66 moves the float ball 62 from a freely floating configuration to a held configuration on the free end 54 of the flexible section 50. An air burst or simply unwinding allows the float ball 62 to separate from the flexible section 50 to the fluid boundary of the two fluids. Flexible tubing with or without coaxial cable is the means to connect 68 the float ball 62 to the means for actuating 66 so that the released and retracted positions of the float ball 62 can be triggered under user control. FIG. 3 shows the antenna element 64 attached to the float ball 62 so that the flexible tubing can attach to the antenna element 64 instead of the float ball 62. Alternatively, the flexible tubing could pass through the antenna element 64 to still attach to the float ball 62. Furthermore, other sensors, besides an antenna element, could be mounted to the float ball 62. When the means for connecting is coaxial cable or at least includes coaxial cable, then the coaxial cable can serve a dual purpose for connecting the float ball 62 and communicating electronically with the antenna element 64.

Embodiments of the present invention include the method of measuring fluids by installing a probe (an antenna element on a float ball) in a tank or vessel. The method includes installing the seal housing 22, the tool assembly 40, and the float assembly 60 in the vessel 12, when the vessel comprises an inlet, an outlet, and a drain pipe 14 having a first end 16, a second end 18 opposite the first end, and a tank block valve 20 on the second end. The tank block valve 20 is an overall control valve to control draining through the drain pipe 14. The step of installing can include closing the tank block valve 20, inserting the float assembly 60 and the flexible section 50 of the tool assembly 40 into the drain pipe 14, and attaching the first flanged end 24 to the second end 18 of the drain pipe 14, when the distal end 44 of the shaft section 40 reaches the drain pipe 14. In this manner, the float ball 62 is within the drain pipe 14 and beyond the seal housing valve 28 of the seal housing 22. Next, the remaining components of the seal housing 22 are connected, and the shaft section 42 inserts through the seal housing valve 28, the second flanged end 26, and the bypass fitting 30. The seal housing valve 28 blocks the float ball 62 from movement toward the shaft housing 34.

The method further includes filling the vessel 12 with at least two fluids 72, 74 and settling the at least two fluids 72, 74 in layers so as to form a fluid layer boundary 70 as indicated in FIGS. 1 and 4. The vessel 12 can be filled before installing the seal housing 22 with the tank block valve 20 closed. Alternatively, the vessel 12 can be filled after installing the seal housing 22 so that the tank block valve 20 does not have to be closed.

Embodiments of the method further include setting the proximal end 46 of the shaft section 42 at a bend 45 between the first end 16 and the second end 18, as in FIGS. 1 and 4. The flexible section 50 extends through the first end 16, and the first end 16 is below the fluid boundary 70. Next, the float ball 62 is released from the free end 54 of the flexible section 50 in order to settle at the fluid boundary 70. In this position, different characteristics of the two fluids can be detected with the antenna element 64 or other sensors. According to dimensions of the vessel 12 and flow rates through the vessel 12, the fluids 72, 74 can be measured. In one embodiment, transmitting location of the float ball 62 relative to the vessel 12 can determine respective amounts of fluids 72, 74 within the vessel 12. The amount of water and oil can be identified so that draining stops before oil leaves the vessel 12.

The method includes opening the tank block valve 20 and opening the seal housing valve 20. The vessel 12 is being drained through the bypass fitting 30 and the bypass flow assembly 32. The bypass flow assembly 32 can lead to further processing, storage, or release. Measurements along the bypass flow assembly 32 can confirm, verify, or contrast the determinations made by the present invention. In some instances, at least one of the two fluids flows through the bypass flow assembly 32 so as to drain the vessel 12.

In embodiments with the shaft section 42 comprised of a plurality of shaft segments 48, the method includes the step of setting the proximal end 46 of the shaft section 42 by attaching each shaft segment 48 to an adjacent shaft segment 48 with a respective shaft connector 49, and repeating the step of attaching until the float ball 62 and the free end 54 of the flexible section 50 reach a bottom of the vessel 12. In alternate embodiments with the flexible section 50 comprised of a spring, metal spring, or a stainless steel coil, the step of setting the proximal end 46 of the shaft section 42 further comprises inserting the flexible section 50 through the bend 45.

The steps of dispensing and gathering the means for connecting 68 correspond to releasing and retracting the float ball 62. When the means for actuating the float ball 66 is a reel, spool, a pneumatic actuator, compressed air system, or a hydraulic actuator, the means for connecting the float ball 68 is dispensed or gathered relative to the means for actuating 66. In one embodiment with the means for connecting as flexible tubing, the means for actuating 66 can wind or unwind the flexible tubing. Alternatively, the means for actuating 66 can use air pressure to release the float ball, which dispenses flexible tubing from the means for actuating 66. Other known components for releasing and retracting the float ball 62 are within the scope of the present invention.

The present invention provides a system and method for measuring fluids by installing a probe in a tank without altering the tank. The integrity of the tank is preserved, even when the inlet and outlet are located at the top of the vessel. Any tank with a drain pipe, including bent drain pipes of any angle, can be retrofit with the system and method of the present invention. Any size of the drain pipe can be used because of the seal housing and the relationship between the tool assembly and the seal housing valve. Additionally, the shaft housing must accommodate the float ball, the antenna element and the flexible section so that the configurations of released and retracted float ball are supported by the friction fit stop at the seal housing valve. The system of the present invention allows for installing a probe in a tank with drain pipe of any size.

The foregoing disclosure and description of the invention is illustrative and explanatory thereof. Various changes in the details of the illustrated structures, construction and method can be made without departing from the true spirit of the invention.

We claim:

1. A system for measuring fluids, said system comprising:
    a vessel containing at least two fluids, said vessel being comprised of an inlet, an outlet, and a drain pipe having a first end, a second end opposite said first end, and a tank block valve on said second end;
    a seal housing comprising:
        a first flanged end connected to said second end,
        a second flanged end,
        a seal housing valve between said first flanged end 24 and said second flanged end,
        a bypass fitting having two junctions,
        a bypass flow assembly in fluid connection with one junction of said bypass fitting, and
        a shaft housing in fluid connection with a remaining junction of said bypass fitting, said first end being located within said vessel, said second end 18 being at a distal location outside the vessel, said tank block valve being positioned between said vessel and said seal housing;
    a tool assembly removably inserted through said drain pipe, said tool assembly comprising:
        a shaft section having a distal end and proximal end,
        a flexible section at said proximal end of said shaft section, said flexible section having an anchored end attached to said proximal end of the shaft section and a free end opposite the anchored end; and
    a float assembly extending through said tool assembly, said float assembly comprising:
        a float ball releasably engaged to said free end of said flexible section,
        an antenna element attached to said float ball,
        a means for actuating said float ball attached to said distal end of said shaft section, and
        a means for connecting said float ball to said means for actuating said float ball, said means for connecting said float ball to said means for actuating said float ball extending through said flexible section and said shaft section,
    wherein a length of said shaft housing of said seal housing accommodates said float ball, said antenna element, and said flexible section of said tool assembly.

2. The system for measuring fluids, according to claim 1, wherein said vessel is further comprised of a sump, said first end being positioned within said sump.

3. The system for measuring fluids, according to claim 1, wherein said drain pipe is bent, said first end being angled downward from said second end.

4. The system for measuring fluids, according to claim 3, said first end being bent 90 degrees downward from said second end.

5. The system for measuring fluids, according to claim 1, wherein said shaft section is comprised of a plurality of shaft segments, each shaft segment being in fluid connection with an adjacent shaft segment and attached to a respective adjacent shaft segment by a shaft connector.

6. The system for measuring fluids, according to claim 1, further comprising:
    a plurality of O-rings on said ends of each shaft connector, each shaft connector being sealed to respective shaft segments.

7. The system for measuring fluids, according to claim 1, wherein said flexible section is comprised of at least one of a group consisting of a spring, metal spring, and a stainless steel coil.

8. The system for measuring fluids, according to claim 1, wherein said means for actuating said float ball is selected from at least one of a reel, spool, a pneumatic actuator, compressed air system, and a hydraulic actuator.

9. The system for measuring fluids, according to claim 1, wherein said means for connecting said float ball is selected from at least one of flexible tubing and coaxial cable.

10. The system for measuring fluids, according to claim 1, wherein said means for connecting said float ball attaches to said antenna element.

11. The system for measuring fluids, according to claim 10, wherein said means for connecting said float ball attaches said coaxial cable to said antenna element, when said means for connecting said float ball is comprised of coaxial cable.

12. A method of measuring fluids, the method comprising the steps of:
    installing said seal housing, said tool assembly, and said float assembly in said vessel, according to claim 1;
    wherein said vessel comprises an inlet, an outlet, and a drain pipe having a first end, a second end opposite said first end, and a tank block valve on said second end, wherein the step of installing comprises:
        closing said tank block valve,
        inserting said float assembly and said flexible section of said tool assembly into said drain pipe, attaching said first flanged end to said second end of said drain pipe, when said distal end of said shaft section reaches said drain pipe, connecting said first flanged end, said seal housing valve, said second flanged end, and said bypass fitting, said shaft section being insertable through said seal housing valve, said second flanged end, and said bypass fitting, said seal housing valve blocking said float ball from movement toward said shaft housing;

filling a vessel with at least two fluids;

settling the at least two fluids in layers so as to form a fluid layer boundary;

setting said proximal end of said shaft section at a bend between said first end and said second end, said flexible section extending through said first end, said first end being below said fluid boundary;

releasing said float ball from said free end of said flexible section;

settling said float ball at said fluid boundary; and detecting characteristics of the two fluids with said antenna element and according to dimensions of said vessel and flow rates through said vessel.

13. The method for measuring fluids, according to claim 12, further comprising the step of:

transmitting location of said float ball relative to the vessel so as to determine respective amounts of fluids within the vessel.

14. The method for measuring fluids, according to claim 12, wherein said bend of said drain pipe is 90 degrees downward.

15. The method for measuring fluids, according to claim 12, wherein said shaft section is comprised of a plurality of shaft segments, each shaft segment being in fluid connection with an adjacent shaft segment and attached to a respective adjacent shaft segment by a shaft connector, said step of setting said proximal end of said shaft section further comprising:

attaching each shaft segment to an adjacent shaft segment with a respective shaft connector, and repeating the step of attaching until said float ball and said free end of said flexible section reaches a bottom of said vessel.

16. The method for measuring fluids, according to claim 12, wherein said flexible section is comprised of at least one of a group consisting of a spring, metal spring, stainless steel coil, said step of setting said proximal end of said shaft section further comprising:

inserting said flexible section through said bend.

17. The method for measuring fluids, according to claim 12, wherein said means for actuating said float ball is selected from at least one of a reel, spool, a pneumatic actuator, compressed air system, and a hydraulic actuator, wherein said means for connecting said float ball is selected from at least one of flexible tubing and coaxial cable, and wherein the step of releasing said float ball comprises:

dispensing means for connecting from said means for actuating.

18. The method for measuring fluids, according to claim 12, wherein said means for actuating said float ball is selected from at least one of a reel, spool, a pneumatic actuator, compressed air system, and a hydraulic actuator, wherein said means for connecting said float ball is selected from at least one of flexible tubing and coaxial cable, and wherein the step of releasing said float ball comprises:

gathering means for connecting to said means for actuating.

19. The method for measuring fluids, according to claim 12, further comprising the steps of:

opening said tank block valve; and opening said seal housing valve.

20. The method for measuring fluids, according to claim 19, further comprising the step of:

flowing at least one of said two fluids through said bypass flow assembly so as to drain said vessel.

* * * * *